US00PP14566P29

(12) United States Plant Patent
Brand

(10) Patent No.: US PP14,566 P2
(45) Date of Patent: Feb. 24, 2004

(54) CEANOTHUS PLANT NAMED 'BRASS'

(50) Latin Name: ***Ceanothus griseus* var. *horizontalis***
Varietal Denomination: Brass

(76) Inventor: Peter Anthony Brand, A. Brand + Sons, Bulls Lane, Bell Bar, Hatfield, Hertfordshire AL9 7BB (GB)

( * ) Notice: Subject to any disclaimer, the term of this patent is extended or adjusted under 35 U.S.C. 154(b) by 0 days.

(21) Appl. No.: 10/173,287

(22) Filed: Jun. 17, 2002

(51) Int. Cl.[7] ..... A01H 5/00
(52) U.S. Cl. ..... Plt./226
(58) Field of Search ..... Plt./226, 248

*Primary Examiner*—Bruce R. Campell
*Assistant Examiner*—Louanne Krawczewicz Myers

(57) ABSTRACT

A new cultivar of Ceanothus named 'Brass' that is characterized by variegated grey-green foliage with cream-white irregularly spotted margins, a spreading habit and small clusters of contrasting pale blue flowers in late spring. In combination these traits set 'Brass' apart from all other existing varieties of Ceanothus known to the inventor.

2 Drawing Sheets

Genus: Ceanothus.
Species: *griseus* var. *horizontalis.*
Denomination: Brass.

BACKGROUND OF THE INVENTION

The present invention relates to a new and distinct cultivar of Carmel Ceanothus that is grown for use as a medium-sized evergreen shrub. The new cultivar is known botanically as a *Ceanothus griseus* var. *horizontalis* and will be referred to hereinafter by the cultivar name 'Brass'.

In 1995 the inventor discovered a spontaneously occurring, variegated branch sport in a cultivated area of Hatfield, England on *Ceanothus griseus* var. *horizontalis* 'Yankee Point' (unpatented). In 1995, the inventor rooted and grew the said variegated branch sport. In 1996 the inventor examined the resulting plant and identified a branch which exhibited improved qualities of expressed variegation, namely a more uniform representation of the cream-white variegation within each leaf. The inventor cut and rooted this branch. From 1997 until 1999, the inventor took all available cuttings from the plants grown-on from the 1996 selection, and thereby built up a population of plants which all exhibited, to varying degrees, a variegation of the type first discovered by the inventor. Thus, the essential characteristic of variegation was considered by the inventor to have been firmly established.

In 2000, the inventor selected Brass as a single plant for subsequent vegetative propagation and eventual commercial introduction. The selection of Brass from the population was based on its overall appearance and qualities of plant habit and expression of variegation. Thus, although 'Yankee Point' may be deemed as the ultimate parent of Brass, the immediate parent is an unnamed one of many unnamed plants resulting from the extraction, propagation and multiplication of the initial 1995 variegated branch sport discovery.

The distinguishing characteristic of 'Brass' is its foliage which appears as a variegated combination of the same grey-green color that is typical of 'Yankee Point' together with irregularly spotted cream-white margins. Otherwise, Brass exhibits the same spreading habit, medium size and small clusters of pale blue flowers that bloom in late spring as are typical of 'Yankee Point' which is the closest comparison plant within the species.

'Brass' is suitable for use in temperate climates as an ornamental patio plant or contrast plant in a perennial border, and will survive mild winters.

'Brass' was first asexually propagated by the inventor in Hatfield, England in 2000 using vegetative tip cuttings. The distinguishing characteristics of foliage variegation have been determined to be stable and uniform within the definitions of range described herein.

SUMMARY OF THE INVENTION

The following represent the distinguishing characteristics of the new Ceanothus cultivar 'Brass'. In combination these traits set 'Brass' apart from all other existing varieties of Ceanothus known to the inventor. 'Brass' has not been tested under all possible conditions and phenotypic differences may be observed with variations in environmental, climatic, and cultural conditions, however, without any variance in genotype.

1. Ceanothus 'Brass' exhibits variegated foliage that is grey-green with irregularly spotted cream-white margins.
2. Ceanothus 'Brass' is a medium sized evergreen shrub that will eventually spread to 120 cm. in width and 175 cm. in height at maturity.
3. Ceanothus 'Brass' exhibits small clusters of pale blue flowers in late spring.
4. Ceanothus 'Brass' is an ornamental shrub used effectively as an accent plant in containers or as a contrast plant in perennial borders.
5. Ceanothus 'Brass' is suitable for temperate climates and will survive mild winters.

BRIEF DESCRIPTION OF THE DRAWINGS

The accompanying color drawings illustrate the overall appearance of the new variety 'Brass', showing colors as true as it is reasonably possible to obtain in colored reproductions of this type. Colors in the drawing may differ from the color values cited in the detailed botanical description which accurately describe the actual colors of the new variety 'Brass'.

The plants illustrated were grown out-of-doors in a cultivated area in Hatfield, England.

The drawing on sheet 1 is a close-up view of the foliage and flowers of 'Brass'.

The drawing on sheet 2 is a view of a whole plant in the landscape showing the plant form and habit.

BOTANICAL DESCRIPTION OF THE PLANT

The following is a detailed description of the Ceanothus cultivar named 'BRASS'. Data was collected in Arroyo Grande, Calif., and from the inventor and from two-year-old plants in two-liter containers grown out-of-doors in both California and England. Phenotypic differences may be observed with variations in environmental, climatic, and cultural conditions, without however, any difference in genotype. Color determinations are in accordance with The Royal Horticultural Society Colour Chart except where general color terms of ordinary dictionary significance are used. The growing requirements are similar to the species.

Botanical classification: Ceanothus 'Brass'.
Species: *griseus* var. *horizontalis.*
Common name: Carmel Ceanothus.
Use: Ornamental.
Commercial classification: Shrub.
Parentage: The parent of 'Brass' is an unnamed plant from a population of plants that resulted from vegetative propagation cycles of the branch sport from *Ceanothus griseus* var. *horizontalis* 'Yankee Point'.
Growth rate: Vigorous. Grows approximately 10 cm. the first year and 35–50 cm. the second year.
Habit: Spreading.
Shape: Pyramidal.
Height (at maturity): 150–175 cm. in height.
Width (at maturity): 80–120 cm. in width.
Hardiness: USDA Zone 8.
Propagation: Vegetative tip cuttings.
Root system: Fine to fibrous.
Soil: Plant in well-drained soils.
Sunlight: Plant in semi-shade or full sun.
Sexuality: Monoecious.
Time to initiate roots: Approximately 2 months are required for an initial cutting to produce roots.
Crop time: Approximately 2 years is required to produce a commercial sized plant from a rooted cutting.
Branching habit: Freely branching.
Seasonal interest: Flowers in spring and variegated foliage year round.
Disease resistance and susceptibility: No more susceptible to pests or disease than similar species.
Stem:
- *Internode length* (*lateral stems*).—Average is 0.9 cm. between nodes.
- *Angle at emergence.*—Lateral branches emerge at an average angle of 45° to 60° to vertical branches.
- *Lateral stem diameter.*—2 mm. in diameter.
- *Lateral stem length.*—11 cm. in length.
- *Shape* (*vertical branches and lateral stems*).—A combination of cylindrical and multicostate.
- *Lenticels.*—Absent.
- *Surface* (*vertical branches and lateral stems*).—Densely covered with small (less than 1 mm.) pale brownish-white hairs 156A.
- *Lateral stem color.*—138B.
- *Vertical branch color.*—138B.
- *Vertical branch length.*—30 cm. in length.
- *Vertical branch diameter.*—2 mm. in diameter.
- *Internode length* (*vertical branches*).—2–4 cm. between nodes.

Foliage:
- *Type.*—Evergreen.
- *Leaf arrangement.*—Alternate.
- *Leaf division.*—Simple.
- *Leaf shape.*—Ovate.
- *Leaf base.*—Atttenuate.
- *Leaf apex.*—Acute to obtuse.
- *Leaf venation.*—Pinnate.
- *Vein color* (*adaxial surface*).—146C.
- *Vein color* (*abaxial surface*).—146C.
- *Leaf surface* (*adaxial*).—Young leaves are pubescent while older leaves are glabrous and glossy.
- *Leaf surface* (*abaxial*).—Young and older leaves are matte and pubescent.
- *Leaf attachment.*—Petiolate.
- *Petiole dimension.*—0.50 cm. in length and 1 mm. in diameter.
- *Petiole color.*—138B. Petiole shape: Flattened oval.

Petiole surface: Pubescent.
- *Stipules.*—Absent.
- *Leaf margins.*—Entire to sparsely serrulate, and revolute.
- *Leaf length.*—1.5–3 cm. in length.
- *Leaf width.*—0.75–1.5 cm. in width.
- *Leaf color* (*adaxial surface*).—Grey-green centers that are a combination of 139A and 191B with cream-white irregularly spotted margins that are combination of 4D and 160B.
- *Leaf color* (*abaxial surface*).—Grey-green centers that are a combination of 189A and 191A with cream-white irregularly spotted margins that are a combination of 160C and 4D.
- *Foliar fragrance.*—Absent.

Flower:
- *Inflorescence.*—Dense panicle.
- *Quantity of inflorescences.*—Approximately 12–15 panicles per branch.
- *Shape of inflorescence.*—Short and rounded.
- *Dimensions of panicle.*—1.75 cm. in length and 1.25 cm. in width.
- *Flower shape.*—Campanulate.
- *Aspect.*—Facing outward.
- *Flower color.*—A combination of 96C and 95D.
- *Color of petal* (*adaxial surface*).—96C.
- *Color of petal* (*abaxial surface*).—95D.
- *Petals.*—Five in number.
- *Petal shape.*—Spatulate.
- *Petal apex.*—Rounded.
- *Petal base.*—Attenuate.
- *Petal margin.*—Entire.
- *Petal surface.*—Smooth.
- *Petal length.*—2.75 mm in length.
- *Petal width.*—Less than 1 mm in width.
- *Unfused or fused.*—Petals are unfused.
- *Bud color.*—95C.
- *Bud shape.*—Globular to flattened globular.
- *Bud dimensions.*—1.00 mm. in length and 2.00 mm. in diameter.
- *Dimensions of open flower.*—3 mm. in diameter and 3 mm. in length.

*Persistent or self-cleaning.*—Self-cleaning.
*Shape of calyx.*—Globose when closed and stellate when open.
*Color of calyx* (*adaxial surface*).—95D.
*Color of calyx* (*abaxial surface*).—95D.
*Dimensions of calyx.*—3 mm. in diameter and 2 mm. in length.
*Number of sepals.*—Five sepals.
*Sepal color* (*adaxial surface*).—95D.
*Sepal color* (*abaxial surface*).—95D.
*Sepal apex.*—Acute.
*Sepal surfaces* (*adaxial and abaxial*).—Glabrous.
*Sepals fused or unfused.*—Basally fused.
*Sepal base.*—Truncate.
*Sepal margin.*—Entire.
*Sepal shape.*—Deltoid.
*Dimensions of sepal.*—Less than 0.75 mm. in width and 2 mm. in length.
*Blooming period.*—May to June.
*Quantity of flowers.*—Approximately 100 flowers per inflorescence.
*Peduncle dimensions.*—5.50–6 cm. in length and 2 mm. in width.
*Color of peduncle.*—144 A.
*Surface of peduncle.*—Puberulent.
*Pedicel dimensions.*—4 mm. in length and 0.50 mm. in diameter.
*Pedicel color.*—95C.
*Pedicel surface.*—Glabrous.
*Fragrance.*—Slightly sweet.

Reproduction organs:
*Stamens.*—Five in number.
*Form of stamen.*—Filament.
*Color of stamens.*—95C.
*Dimensions of stamen.*—4 mm. in length and less than 0.25 mm in diameter.
*Dimensions of anther.*—0.50 mm. in width and 1 mm. in length.
*Color of anther.*—11B.
*Pollen color.*—11B.
*Quantity of pollen.*—Moderate amount.
*Pistil.*—One in number.
*Pistil shape.*—Columnar.
*Dimensions of pistil.*—3 mm. in length and less than 0.50 mm. in diameter.
*Stigma shape.*—Trifid.
*Stigma color.*—98B.
*Dimensions of stigma.*—1 mm. in height and 1.25 mm. in diameter.
*Style color.*—95C.
*Style dimensions.*—1 mm. in length and less than 0.50 mm. in diameter.
*Ovary position.*—Superior.
*Ovary color.*—202A.
*Ovary dimensions.*—2 mm. in diameter and 1 mm. in height.
*Ovary shape.*—Flattened globular.

Seed:
*Fruit color.*—202A.
*Fruit surface.*—Glossy when mature.
*Fruit shape.*—3-lobed capsule.
*Length of fruit.*—4 mm. in length.
*Fruit texture.*—Granular and sticky.
*Number of seeds.*—100 per inflorescence.
*Seed shape.*—Globular.
*Seed color.*—202A.
*Seed dimensions.*—2 mm. in diameter and 2 mm. in length.

I claim:

1. A new and distinct variety of Ceanothus plant named 'Brass' as described and illustrated.

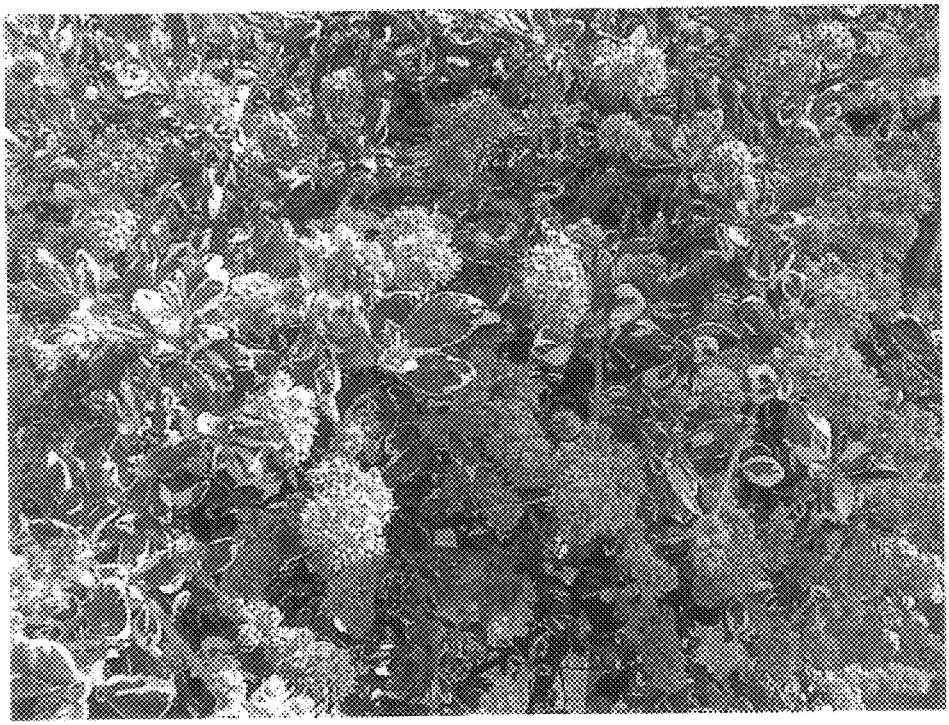

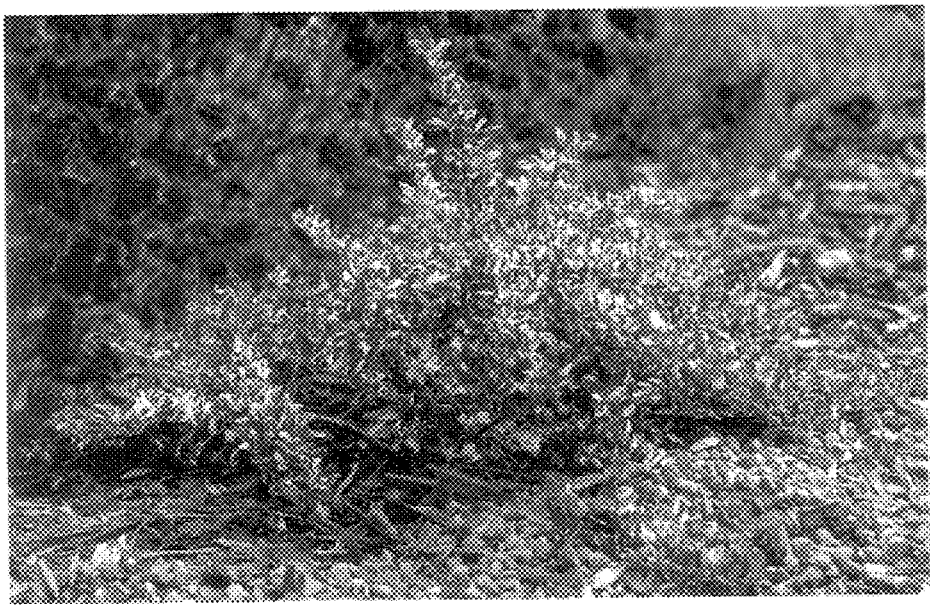

* * * * *